US00PP12122P2

(12) United States Plant Patent
Miyazaki

(10) Patent No.: US PP12,122 P2
(45) Date of Patent: Oct. 2, 2001

(54) SENECIO GENUS PLANT NAMED 'SUNSENEREBA'

(75) Inventor: Kiyoshi Miyazaki, Hikone (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/347,231

(22) Filed: Jul. 2, 1999

(51) Int. Cl.[7] ..... A01H 5/00
(52) U.S. Cl. ..... Plt./263
(58) Field of Search ..... Plt./263

(56) References Cited

PUBLICATIONS

Asteraceae Cladistics & Classifications, K. Bremer, 1994, p. 508.*

* cited by examiner

*Primary Examiner*—Bruce R. Campell
*Assistant Examiner*—Anne Marie Grünberg

(74) *Attorney, Agent, or Firm*—Burns, Doane, Swecker & Mathis, L.L.P.

(57) ABSTRACT

Disclosed herein is a Senecio genus plant named 'Sunsenereba' which is a tall dome-shaped plant with abundant branching. There are very few pubescences on its stems. The leaf length of 'Sunsenereba' is shorter and the petiole is longer than that in other varieties of *Senecio L.* 'Sunsenereba' has no stipule. The flower cluster is large. The flower is single flowered having a wide white central part. The petal has a vivid purple tip and a white base. The disk flower is deep reddish purple. The blooming starts early and the blooming term is longer than *Senecio cruentus*. Flower buds grow one after another from axil. 'Sunsenereba' is distinguished from other varieties particularly by (A) being tall, dome-shaped with abundant branching, (B) having very sparse pubescences on its stems, (C) having short leaves and a long petiole, (D) having a large flower cluster, (E) having vivid reddish purple petals and deep reddish purple disk flowers, (F) having flowers with side white marginal parts, (G) having a long blooming term and (H) having low fertility.

2 Drawing Sheets

BACKGROUND OF THE VARIETY

The present invention relates to a new and distinct variety of Senecio genus plant named 'Sunsenereba', which is a relatively tall, dome-shaped plant with abundant branching, vivid reddish purple flowers having white marginal parts and a long blooming term.

There are many varieties of *Senecio L. Senecio cruentus* is well known as Cineraria and cultivated in the world. There are many cultivated varieties. Flowers of Senecio are of a solid color of white, pink red, blue or violet. Some varieties have marginal variegation with off color parts.

The female parent used in the crossing of 'Sunsenereba' is a cultivar, *Senecio cruentus*, 'Jupiter Pink-white' (not patented in the United States). 'Jupiter Pink-white' is a compact, dome-shaped plant, 17.5 cm in height. the stem is thick, 8.0 mm in diameter, with anthocyanin coloration. The leaf is of a serrated heart form and moderate yellowish green. The leaf size is medium, 11.5 cm long and 12.5 cm wide. The flower is single flowered and has light pink petals with deep pink disk flowers and distinct white marginal parts. 'Jupiter Pink-white' has some scent.

The pollen parent used in the crossing of 'Sunsenereba' is *Senecio heritierii* (not patented in the United States), which was introduced from nurseries in England. *Senecio heritierii* is a tall, dome-shaped plant, 26 cm in height with abundant branching. The stem is 5.1 mm in diameter, with no anthocyanin coloration. The leaf is of a serrated heart form and light yellowish green. The leaf is small, 5.5 cm long and 6.3 cm wide. The flower is single flowered, has strong purple petals with vague white parts and strong reddish purple disk flowers. *Senecio heritierii* has no scent.

The controlled crossing with *Senecio cruentus* 'Jupiter Pink-white' and *Senecio heritierii* was first conducted at Hakushu-cho, Kitokoma-gun, Yamanashi-ken, Japan in January 1995. Seedlings from this crossing were grown since July 1955. One variety was selected in January 1996 among them in view of flower color and early blooming. After multiplication by tissue culture, the botanical characteristics of the selected variety were examined and tested in potting, using parental varieties, as well as 'Rouge Chigasaki', 'Miss Yokohama', and 'Midget', for comparison since July 1996. As a result, it has been confirmed that this selected variety is uniform and stable in its characteristics.

This new variety of Senecio genus plant was named 'Sunsenereba' (*Senecio cruentus*×*Senecio heritierii*).

*Senecio cruentus* 'Jupiter Pink-white', and *Senecio heritierii* are presently maintained at Hakushu-cho, Kitokoma-gun, Yamanashi-ken, Japan.

In the following descriptions, the color-coding is in accordance with The Horticultural Colour Chart of The Royal Horticultural Society, London. England (R.H.S. Colour Chart) and the color chart based on The Japan Color Standard for Horticultural Plant (J.H.S. Color Chart).

The botanical characteristics of the female parent plant *Senecio cruentus,* 'Jupiter Pink-white' used in the crossing of 'Sunsenereba' are as follows.

Plant:
- *Growing habit.*—Dwarf compact.
- *Height.*—17.5 cm.

Stem:
- *Thickness.*—8.0 mm.
- *Color.*—Moderate yellowish green (R.H.S.C.C. No. 139C, J.H.S.C.C. No. 3709).

*Anthocyanin coloration.*—Present.
*Degree of anthocyanin coloration.*—Medium.
*Branching.*—Few.
*Type of primary lateral shoot.*—Branch from every node.
*Pubescence.*—Dense.
*Length of internode.*—0.6 cm.

Leaf:
*Whole shape.*—Heart form with a swollen basal part, which is notched at where the basal part attaches to a petiole.
*Depth of concavity of leaf margin.*—Shallow.
*Type of convexity.*—Acute.
*Apex-shape.*—Obtuse.
*Base shape.*—Cordate.
*Degree of undulation.*—Fair.
*Length.*—11.5 cm.
*Width.*—12.5 cm.
*Diameter of petiole.*—5.6 mm.
*Length of petiole.*—5.2 cm.
*Stipule.*—Absent.
*Color of upper surface.*—Moderate yellowish green (R.H.S.C.C. No. 137D, J.H.S.C.C. No. 3712).
*Color of reverse surface.*—Grayish yellowish green (R.H.S.C.C. No. 138B, J.H.S.C.C. No. 3715).
*Anthocyanin coloration of reverse surface.*—Present.
*Degree of anthocyanin coloration.*—Light.
*Pubescence of upper surface.*—Present.
*Pubescence of reverse surface.*—Dense.
*Color of pubescence of reverse surface.*—White.

Flower (single flowered):
*Shape of flower cluster.*—Flat.
*Diameter of flower cluster.*—18 cm.
*Height of flower cluster.*—10 cm.
*Transected shape of corolla.*—Flat.
*Diameter of flower.*—5.5 cm.
*Size of disk flower.*—1.5 cm.
*Color of petal.*—Light pink (R.H.S.C.C. No. 48D, J.H.S.C.C. No. 0403).
*Marginal variegation.*—Present.
*Diameter of off color part.*—2.5 cm.
*Border of marginal variegation.*—Distinct.
*Color of disk flower.*—Deep pink (R.H.S.C.C. No. 47C, J.H.S.C.C. No. 0405).
*Petal length.*—2.5 cm.
*Petal width.*—0.8 cm.
*Shape of petal.*—Rectangular.
*Lengthwise warp of petal.*—Convex.
*Concavity of petal tip.*—Present.
*Shape of petal tip.*—Rounded.
*Number of ray flower.*—13.
*Number of disk flower.*—110.
*Diameter of pedicel of the first flower in a blooming period (the flower was attached to the top of a stem).*—1.5 mm.
*Length of pedicel of the first flower in a blooming period (the flower was attached to the top of a stem).*—2.4 cm.
*Number of flowers per flower cluster.*—60.
*Scent.*—Present.

Calyx:
*Degree of concavity.*—Flat.
*Degree of recurvature.*—2.1 mm.
*Color.*—Moderate yellowish green (R.H.S.C.C. No. 139D, J.H.S.C.C. No. 3703).
*Anthocyanin coloration.*—Absent.

Pistil:
*Color.*—Deep pink (R.H.S.C.C. No. 47C, J.H.S.C.C. No. 0405).
*Number.*—1.
*Type.*—The top of the style is splitted into two and the shape of the top is truncated.

Stamen:
*Color.*—Deep pink (R.H.S.C.C. No. 47C, J.H.S.C.C. No. 0405).
*Type.*—5 anthers are connate, with separated filaments.
*Blooming period.*—December (Sowing in August).

Hardiness:
*Cold.*—Good.
*Heat.*—Good.

Resistance:
*Disease.*—Good.
*Insect.*—Good.

The botanical characteristics of the male parent plant *Senecio heritierii* (not patented in the United States) used in the crossing of 'Sunsenereba' are as follows.

Plant:
*Growth habit.*—Semi-dwarf erect.
*Height.*—26 cm.

Stem:
*Thickness.*—5.1 mm.
*Color.*—very pale green (R.H.S.C.C. No. 128D, J.H.S.C.C. No. 4902).
*Anthocyanin coloration.*—Absent.
*Branching.*—Abundant.
*Type of primary lateral shoot.*—Branch from every mode.
*Pubescence.*—Dense.
*Length of internode.*—0.8 cm.

Leaf:
*Whole shape.*—Heart form with a swollen basal part, which is notched at where the basal part attaches to a petiole.
*Depth of concavity of leaf margin.*—Medium.
*Type of convexity.*—Acute.
*Apex shape.*—Obtuse.
*Base shape.*—Cordate.
*Degree of undulation.*—Weak.
*Length.*—5.5 cm.
*Width.*—6.3 cm.
*Diameter of petiole.*—3.5 mm.
*Length of petiole.*—7.5 cm.
*Stipule.*—Absent.
*Color of upper surface.*—Light yellowish green (R.H.S.C.C. No. 136D, J.H.S.C.C. No. 4002).
*Color of reverse surface.*—Very pale green (R.H.S.C.C. No. 128D, J.H.S.C.C. No. 4902).
*Anthocyanin coloration of reverse surface.*—Absent.
*Pubescence of upper surface.*—Dense.
*Pubescence of reverse surface.*—Dense.
*Color of pubescence of reverse surface.*—White.

Flower (single flowered):
*Shape of flower cluster.*—Uneven.
*Diameter of flower cluster.*—18 cm.
*Height of flower cluster.*—15 cm.
*Transected shape of corolla.*—Flat.
*Diameter of flower.*—4.8 cm.

*Size of disk flower.*—0.9 cm.
*Color of petal.*—Strong purple (R.H.S.C.C. No. 81B, J.H.S.C.C. No. 8605).
*Marginal variegation.*—Present.
*Diameter of off color part.*—1.3 cm.
*Border of marginal variegation.*—Vague.
*Color of disk flower.*—Strong reddish purple (R.H.S.C.C. No. 72A, J.H.S.C.C. No. 9214).
*Petal length.*—2.2 cm.
*Petal width.*—0.4 cm.
*Shape of petal.*—Rectangular.
*Lengthwise warp of petal.*—Flat.
*Concavity of petal tip.*—Present.
*Shape of petal tip.*—Acute.
*Number of ray flower.*—13.
*Number of disk flower.*—110.
*Diameter of pedicel of the first flower in a blooming period (the flower was attached to the top of a stem).*—1.2 mm.
*Length of pedicel of the first flower in a blooming period (the flower was attached to the top of a stem).*—2.5 cm.
*Number of flowers per flower cluster.*—35.
*Scent.*—Absent.

Calyx:
*Degree of concavity.*—Flat.
*Degree of recurvature.*—3.1 mm.
*Color.*—Very pale green (R.H.S.C.C. No. 128D, J.H.S.C.C. No. 4902).
*Anthocyanin coloration.*—Present.

Pistil:
*Color.*—Strong reddish purple (R.H.S.C.C. No. 72A, J.H.S.C.C. No. 9214).
*Number.*—1.
*Type.*—The top of the style is splitted into two and the shape of the top is truncated.

Stamen:
*Color.*—Strong reddish purple (R.H.S.C.C. No. 72A, J.H.S.C.C. No. 9214).
*Type.*—5 anthers are connate, with separated filaments.
*Blooming period.*—End of January (Sowing in August).

Hardiness:
*Cold.*—Good.
*Heat.*—Good.

Resistance:
*Disease.*—Good.
*Insect.*—Good.

The botanical characteristics of the similar variety 'Rouge Chigasaki' (not patented in the United States) used for examination as a comparison variety are as follows.

Plant:
*Growth habit.*—Dwarf.
*Height.*—17.5 cm.

Stem:
*Thickness.*—9.1 mm.
*Color.*—Moderate purplish red (R.H.S.C.C. No. 130D, J.H.S.C.C. No. 4302).
*Anthocyanin coloration.*—Present.
*Degree of anthocyanin coloration.*—Medium.
*Branching.*—Moderate in number.
*Type of primary lateral shoot.*—Branch from every node.
*Pubescence.*—Dense.
*Length of internode.*—0.8 cm.

Leaf:
*Whole shape.*—Heart form with a swollen basal part, which is notched at where the basal part attaches to a petiole.
*Depth of concavity of leaf margin.*—Medium.
*Type of convexity.*—Acute.
*Apex shape.*—Medium.
*Base shape.*—Cordate.
*Degree of undulation.*—Fair.
*Length.*—12.1 cm.
*Width.*—13.7 cm.
*Diameter of petiole.*—6.1 mm.
*Length of petiole.*—6.1 cm.
*Stipule.*—Absent.
*Color of upper surface.*—Moderate yellowish green (R.H.S.C.C. No. 137C, J.H.S.C.C. No. 3712).
*Color of reverse surface.*—Moderate yellowish green (R.H.S.C.C. No. 146C, J.H.S.C.C. No. 3312).
*Anthocyanin coloration of reverse surface.*—Absent.
*Pubescence of upper surface.*—Present.
*Pubescence of reverse surface.*—Dense.
*Color of pubescence of reverse surface.*—White.

Flower (single flowered):
*Shape of flower cluster.*—Rounded.
*Diameter of flower cluster.*—22 cm.
*Height of flower cluster.*—13 cm.
*Transected shape of corolla.*—Flat.
*Diameter of flower.*—3.8 cm.
*Size of disk flower.*—1.1 cm.
*Color of petal.*—Deep red (R.H.S.C.C. No. 60B. J.H.S.C.C. No. 0108).
*Marginal variegation.*—Present.
*Diameter of off color part.*—3 cm.
*Border of marginal variegation.*—Vague.
*Color of disk flower.*—Deep purplish red (R.H.S.C.C. No. 61A, J.H.S.C.C. No. 9710).
*Petal length.*—1.3 cm.
*Petal width.*—1.1 cm.
*Shape of petal.*—Elliptical.
*Lengthwise warp of petal.*—Convex.
*Concavity of petal tip.*—Present.
*Shape of petal tip.*—Rounded.
*Number of ray flower.*—13–14.
*Number of disk flower.*—107.
*Diameter of pedicel of the first flower in a blooming period (the flower was attached to the top of a stem).*—1.7 mm.
*Length of pedicel of the first flower in a blooming period (the flower was attached to the top of a stem).*—2.9 cm.
*Number of flowers per flower cluster.*—170.
*Scent.*—Present.

Calyx:
*Degree of concavity.*—Flat.
*Degree of recurvature.*—2.1 mm.
*Color.*—Moderate yellowish green (R.H.S.C.C. No. 139D, J.H.S.C.C. No. 3703).
*Anthocyanin coloration.*—Present.

Pistil:
*Color.*—Deep purplish red (R.H.S.C.C No. 61A, J.H.S.C.C. No. 9710).
*Number.*—1.
*Type.*—The top of the style is splitted into two and the shape of the top is truncated.

Stamen:
*Color.*—Deep purplish red (R.H.S.C.C. No. 61A, J.H.S.C.C. No. 9710).
*Type.*—5 anthers are connate, with separated filaments.
*Blooming period.*—February (Sowing in August).
Hardiness:
*Cold.*—Good.
*Heat.*—Good.
Resistance:
*Disease.*—Good.
*Insect.*—Good.

The botanical characteristics of the similar variety 'Miss Yokohama' (not patented in the United States) used for examination as a comparison variety are as follows.

Plant:
*Growth habit.*—Dwarf compact.
*Height.*—19 cm.
*Spread.*—19 cm.
Stem:
*Thickness.*—5.4 mm.
*Color.*—Moderate yellowish green (R.H.S.C.C. No. 139C., J.H.S.C.C. No. 3709).
*Anthocyanin coloration.*—Present.
*Degree of anthocyanin coloration.*—Medium.
*Branching.*—Moderate in number.
*Type of primary lateral shoot.*—Branch from every node.
*Pubescence.*—Dense.
*Length of internode.*—0.5 cm.
Leaf:
*Whole shape.*—Heart form with a swollen basal part, which is notched at where the basal part attaches to a petiole.
*Depth of concavity of leaf margin.*—Medium.
*Type of convexity.*—Acute.
*Apex shape.*—Medium.
*Base shape.*—Cordate.
*Degree of undulation.*—Weak.
*Length.*—17.5 cm.
*Width.*—13.0 cm.
*Diameter of petiole.*—5.2 mm.
*Length of petiole.*—7.7 cm.
*Stipule.*—Present.
*Color of upper surface.*—Moderate yellowish green (R.H.S.C.C. No. 137C, J.H.S.C.C. No. 3712).
*Color of reverse surface.*—Moderate yellowish green (R.H.S.C.C. No. 138C, J.H.S.C.C. No. 3709).
*Anthocyanin coloration of reverse surface.*—Present.
*Degree of anthocyanin coloration.*—Medium.
*Pubescence of upper surface.*—Dense.
*Pubescence of reverse surface.*—Dense.
*Color of pubescence of reverse surface.*—White.
Flower (single flowered):
*Shape of flower cluster.*—Rounded.
*Diameter of flower cluster.*—23 cm.
*Height of flower cluster.*—17 cm.
*Transected shape of corolla.*—Flat.
*Diameter of flower.*—4.2 cm.
*Size of disk flower.*—1.1 cm.
*Color of petal.*—Vivid violet (R.H.S.C.C. No. 96A, J.H.S.C.C. No. 8005).
*Marginal variegation.*—Present.
*Diameter of off color part.*—2.5 cm.
*Border of marginal variegation.*—Fairly clear.
*Color of disk flower.*—Disk violet (R.H.S.C.C. No. 93A, J.H.S.C.C. No. 8006).
*Petal length.*—1.6 cm.
*Petal width.*—0.8 cm.
*Shape of petal.*—Rectangular.
*Lengthwise warp of petal.*—Convex.
*Concavity of petal tip.*—Present.
*Shape of petal tip.*—Rounded.
*Number of ray flower.*—13.
*Number of disk flower.*—86.
*Diameter of pedicel of the first flower in a blooming period (the flower was attached to the top of a stem).*—1.7 mm.
*Length of pedicel of the first flower in a blooming period (the flower was attached to the top of a stem).*—2.7 cm.
*Number of flowers per flower cluster.*—90.
*Scent.*—Present.
Calyx:
*Degree of concavity.*—Flat.
*Degree of recurvature.*—1.2 mm.
*Color.*—Very pale green (R.H.S.C.C. No. 130D, J.H.S.C.C. No. 4302).
*Anthocyanin coloration.*—Absence.
Pistil:
*Color.*—Deep violet (R.H.S.C.C. No. 93A, J.H.S.C.C. No. 8006).
*Number.*—1.
*Type.*—The top of the style is splitted into two and the shape of the top is truncated.
Stamen: Color Deep violet (R.H.S.C.C. No. 93A, J.H.S.C.C. No. 8006).
*Number.*—1.
*Type.*—5 anthers are connate, with separated filaments.
*Blooming period.*—January (Sowing in August).
Hardiness:
*Cold.*—Good.
*Heat.*—Good.
Resistance:
*Disease.*—Good.
*Insect.*—Good.

The botanical characteristics of the similar variety 'Midget' (not patented in the United States) used for examination as a comparison variety are as follows.

Plant:
*Growth habit.*—Dwarf.
*Height.*—14 cm.
Stem:
*Thickness.*—5.6 mm.
*Color.*—Moderte yellowish green (R.H.S.C.C. No. 139C, J.H.S.C.C. No. 3709).
*Anthocyanin coloration.*—Present.
Degree of anthocyanin coloration:
*Branching.*—Moderate in number.
*Type of primary lateral shoot.*—Branch from every node.
*Pubescence.*—Dense.
*Length of internode.*—0.5 cm.
Leaf:
*Whole shape.*—Heart form with a swollen basal part, which is notched at where the basal part attaches to a petiole.
*Depth of concavity of leaf margin.*—Medium.
*Type of convexity.*—Acute.

*Apex shape.*—Acute.
*Base shape.*—Cordate.
*Degree of undulation.*—Fair.
*Length.*—13.9 cm.
*Width.*—10.3 cm.
*Diameter of petiole.*—4.2 mm.
*Length of petiole.*—4.7 cm.
*Stipule.*—Present.
*Color of upper surface.*—Grayish yellowish green (R.H.S.C.C. No. 138A, J.H.S.C.C. No. 3514).
*Color of reverse surface.*—Grayish yellowish green (R.H.S.C.C. No. 138B, J.H.S.C.C. No. 3115).
*Anthoycanin coloration of reverse surface.*—Absent.
*Pubescence of upper surface.*—Present.
*Pubescence of reverse surface.*—Dense.
*Color of pubescence of reverse surface.*—White.

Flower (single flowered):
*Shape of flower cluster.*—Flat.
*Diameter of flower cluster.*—22 cm.
*Height of flower cluster.*—8 cm.
*Transected shape of corolla.*—Fairly closed.
*Diameter of flower.*—3.2 cm.
*Size of disk flower.*—0.8 cm.
*Color of petal.*—Vivid reddish purple (R.H.S.C.C. No. 74A, J.H.S.C.C. No. 9207).
*Marginal variegation.*—Absent.
*Color of disk flower.*—Strong reddish purple (R.H.S.C.C. No. 72A, J.H.S.C.C. No. 9209).
*Petal length.*—1.5 cm.
*Petal width.*—0.8 cm.
*Shape of petal.*—Elliptical.
*Lengthwise warp of petal.*—Flat.
*Concavity of petal tip.*—Present.
*Shape of petal tip.*—Acute.
*Number of ray flower.*—13.
*Number of disk flower.*—86.
*Diameter of pedicel of the first flower in a blooming period (the flower was attached to the top of a stem).*—1.5 mm.
*Length of pedicel of the first flower in a blooming period (the flower was attached to the top of a stem).*—2.5 cm.
*Number of flowers per flower cluster.*—180.
*Scent.*—Present.

Calyx:
*Degree of concavity.*—Flat.
*Degree of recurvature.*—2.2 mm.
*Color.*—Moderate yellowish green (R.H.S.C.C. No. 139C, J.H.S.C.C. No. 3709).
*Anthocyanin coloration.*—Absent.

Pistil:
*Color.*—Strong reddish purple (R.H.S.C.C. No. 72A, J.H.S.C.C. No. 9209).
*Number.*—1.
*Type.*—The top of the style is splitted into two and the shape of the top is truncated.

Stamen:
*Color.*—Strong reddish purple (R.H.S.C.C. No. 72A, J.H.S.C.C. No. 9209).
*Type.*—5 anthers are connate, with separated filaments.
*Blooming period.*—January (Sowing in August).

Hardiness:
*Cold.*—Good.
*Heat.*—Good.

Resistance:
*Disease.*—Good.
*Insect.*—Good.

SUMMARY OF THE NEW VARIETY

'Sunsenereba' is a relatively tall, dome-shaped plant averaging 30.5 cm in height in the blooming period. It branches from every node and the branching is abundant. The stem is 4.2 mm in diameter, with anthocyanin coloration and sparse pubescences.

The leaf is small, 8.0 cm long and 9.3 cm wide. Its shape is in a serrated heart form with a swollen basal part, which is notched at where the basal part attaches to a petiole. The leaf is strong yellowish green, with light anthocyanin coloration on the reverse side. Pubescence on both sides of the leaf is dense. The petiole is 8.1 cm long and 2.8 mm in diameter.

The flower cluster is large, tall and uneven in shape (i.e. the locations of the heads in the flower cluster is uneven, i.e. irregular, and not flat). The term "flower cluster" refers to a gathering of the heads in a plant. A head or flower of 'Sunsenereba' contains a disk and a plurality of petals, i.e. ray flowers. A disk flower is tubular and has a pistil, but no stamen. A ray flower has a pistil and stamens formed by 5 anthers fused together with separated filaments. The flower is single flowered and has a white central part, which is an off color part at the base of the petal (the off color part is a white part of the flower forming a centrally located circular pattern). The diameter of the off color part is 3.4 cm (i.e. the diameter of the centrally located circular pattern is 3.4 cm) and the border of marginal variegation is fairly clear. The transected shape (i.e. the cross section of the corolla viewed from the side) of the corolla is fairly closed. In other words, when the corolla is open, the petals are slanted slightly upward when a side view of the cross section of the corolla is taken. The flower diameter is 6.7 cm. The petal is 2.9 cm long, 0.8 cm wide and vivid reddish purple. The disk flower is 1.1 cm in diameter and its color is deep reddish purple. One flower has 13 ray flowers and 127 disk flowers. A flower cluster has 97 flowers. The degree of recurvature of the calyx is 2.2 mm. The calyx is flat and has some anthocyanin coloration. The pedicel is 4.5 cm long and 1.2. mm in diameter. The flowers have some scent.

The blooming period is early and the blooming term is long. After cutting in July in Hakusho-cho, Kitakoma-gun, Yamanashi-ken, Japan, 'Sunseneraba' begins to bloom in the first 10 days of December. The plant continues to bloom from December to May under appropriate control. If the temperature is maintained around 15° C., individual blooms last about 2 weeks. Flower buds grow one after another from the axil (when an upper flower finished growing, a flower bud is generated from the next lower axil). The flowers are not self-cleaning, so petals remain attached in a wilted and dry state as a flower fully matures.

'Sunsenereba' has moderate cold hardiness and resistance to heat. It does not die at a temperature around 0° C. When frost occurs, its cells can be necrosed resulting in the death of 'Sunsenereba'. *Senecio cruentus* usually slows down its growth slightly in a hot season. In comparison, 'Sunsenereba' has no problem in growing in the hot season.

Generally, Senecio varieties have high seed fertility, i.e. have many seeds per flower. However, the fertility of 'Sunsenereba' is low. The new variety has no seed or very few seeds per flower. When no seed is formed, there is a part corresponding to a seed coat and only the seed coat part remains in an immature state because there is no embryo and endosperm within the immature seed coat part.

The new variety of Senecio genus plant named 'Sunsenereba' differs from the similar varieties, 'Rouge Chigasaki', 'Miss Yokohama', and 'Midget', as well as the parental varieties, *Senecio heritierii* and 'Jupiter Pink-white', in the following botanical characteristics.

1. 'Sunsenereba' is a tall type plant, 30.5 cm in height. 'Rouge Chigasaki' is a compact type plant, 17.5 cm in height. 'Miss Yokohama' is a compact type plant, 19 cm in height. 'Midget' is a compact type plant, 14 cm in height. The pollen parent '*Senecio heritierii*' is a semi-compact type plant, 26 cm in height. The female parent 'Jupiter Pink-white' is a compact type plant, 17.5 cm in height.

2. The flower of 'Sunsenereba' has petals with a vivid reddish purple tip and white base forming a central white part for the flower, and deep reddish purple disk flowers. That of 'Rouge Chigasaki' has deep red petals with white wide parts, and deep purplish red disk flowers. That of 'Miss Yokohama' has vivid violet petals with wide white parts, and deep violet disk flowers. That of 'Midget' has petals of a solid color, i.e. vivid reddish purple, with no marginal variegation, and deep reddish purple disk flowers. That of female parent 'Jupiter Pink-white' has deep purplish red petals with wide white parts, and moderate purplish red disk flowers. That of pollen parent *Senecio heritierii* has deep purple petals with narrow white parts, and deep reddish purple disk flowers.

3. The leaf of 'Sunsenereba' is shorter than that of 'Rouge Chigasaki', 'Miss Yokohama' or 'Midget'. The petiole is longer than that of 'Rouge Chigasaki'or 'Midget'.

4. 'Sunsenereba' has fewer pubescence of stems then that of 'Rouge Chigasaki', 'Miss Yokohama' or 'Midget'.

5. The blooming term of 'Sunsenereba' is longer than that of 'Rouge Chigasaki', 'Miss Yokohama' or 'Midget'.

6. The fertility of 'Sunsenereba' is lower than that of 'Rouge Chigasaki', 'Miss Yokohama' or 'Midget'.

The plant height, flower color and leaf size are the most distinctive characteristics of this new variety 'Sunsenereba'.

DESCRIPTION OF THE NEW VARIETY

Figure 1:
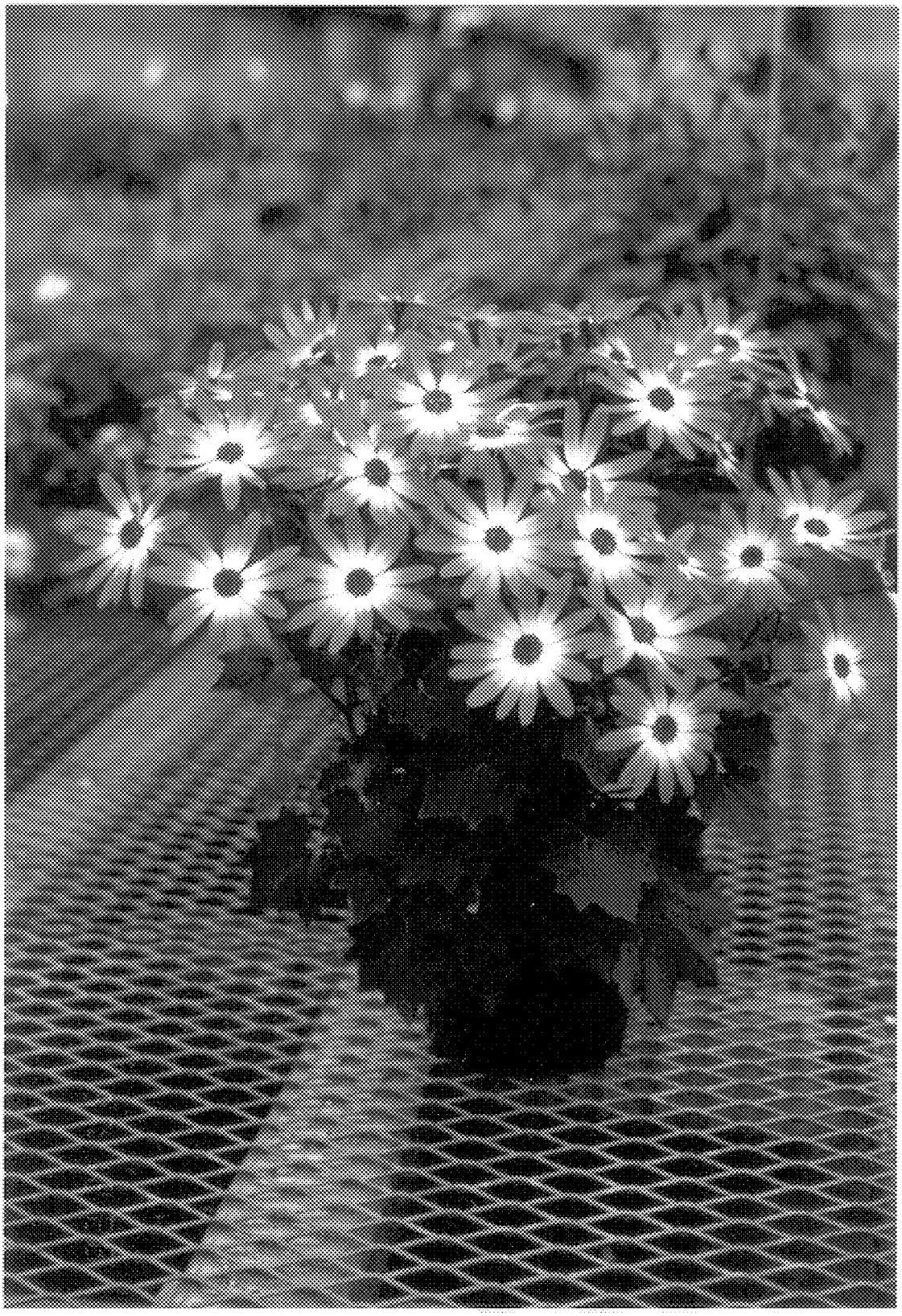
FIG. 1 is a photograph giving a partial view of the new variety of Senecio genus plant named 'Sunsenereba' planted in a pot.
Figure 2:
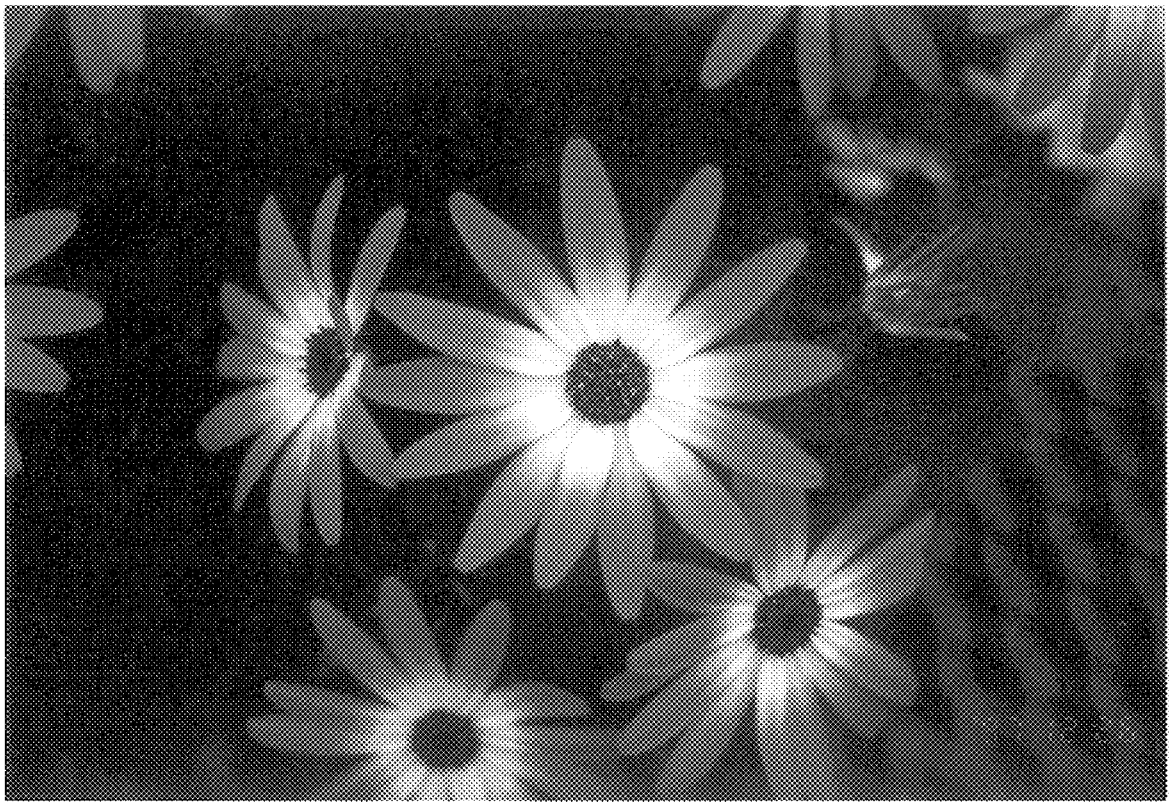
FIG. 2 is a photograph of flowers of the new variety of Senecio genus plant named 'Sunsenereba'.

The botanical characteristics of this new and distinct variety of Senecio genus plant named 'Sunsenereba' are as follows based on observations made 6 months after cutting (cutting was performed in July in Hakushu-cho, Kitakoma-gun, Yamanashi-ken, Japan; the plant was planted in a pot of 15 cm diameter and grown in a green house with the minimum temperature in winter kept at 12° C.; and observations were made in January).

Plant:
- *Growth habit.*—Semi-dwarf erect.
- *Height.*—About 30.5 cm.

Stem:
- *Thickness.*—About 4.2 mm.
- *Color.*—Yellowish green (R.H.S.C.C.No. 148A).
- *Anthocyanin coloration.*—Present.
- *Degree of anthocyanin coloration.*—Medium.
- *Branching.*—Abundant (9 to 11 branches).
- *Type of primary lateral shoot.*—Branch from every node.
- *Pubescence.*—Sparse.
- *Length of internode.*—About 1.2 cm.

Leaf:
- *Whole shape.*—Heart form with a swollen basal part, which is notched at where the basal part attaches to a petiole.
- *Depth of concavity of leaf margin.*—Deep (7 mm).
- *Type of convexity.*—Acute (i.e. there are pointed serrations at the leaf margin).
- *Apex shape.*—Acute.
- *Base shape.*—Cordate.
- *Degree of undulation.*—Weak.
- *Length.*—About 8.0 cm.
- *Width.*—About 9.3 cm.
- *Diameter of petiole.*—About 2.8 mm.
- *Length of petiole.*—About 8.1 cm.
- *Stipule.*—Absent.
- *Color of upper surface.*—Grayish olive green (R.H.S.C.C.No. 137A).
- *Color of reverse surface.*—Moderate yellowish green (R.H.S.C.C.No. 146D, J.H.S.C.C.No. 3110).
- *Anthocyanin coloration of reverse surface.*—Present.
- *Degree of anthocyanin coloration.*—Light.
- *Color of petiole.*—The color of the part near the stem is R.H.S.C.C.No. 59B and that of the part near the blade is R.H.S.C.C.No. 138B.
- *Pubescence of upper surface.*—Dense.
- *Pubescence of reverse surface.*—Dense.
- *Color of pubescence of reverse surface.*—White.

Flower (single flowered):
- *Shape of flower cluster.*—Uneven.
- *Diameter of flower cluster.*—About 38 cm.
- *Height of flower cluster.—About* 19 cm (the height measured from the upper most flower in the flower cluster to the lowest flower is 19 cm).
- *Transected shape of corolla.*—Fairly closed.
- *Diameter of flower.*—About 6.7 cm.
- *Size of disk flower.*—About 1.1 cm.
- *Color of petal.*—The tip of the petal is vivid purple (R.H.S.C.C.No. 81A), while the base of the petal is white (R.H.S.C.C.No. 155B).
- *Marginal variegation.*—Present.
- *Diameter of off color part.*—About 3.4 cm (i.e. the diameter of the white central part of the flower with a disk flower in the middle is about 3.4 cm).
- *Border of marginal variegation.*—Fairly clear (i.e. the border between the vivid purple tip and white base of the petal is fairly clear).
- *Color of disk flower.*—Deep reddish purple (R.H.S.C.C.No. 79B, J.H.S.C.C.No. 8907).
- *Petal length.*—About 2.9 cm (the vivid purple tip of the petal is 1.8 cm long, while the white base of the petal is 1.1 cm long).
- *Petal width.*—About 0.8 cm.
- *Shape of petal.*—Rectangular.
- *Lengthwise warp of petal.*—Flat.
- *Concavity of petal tip.*—Absent.
- *Shape of petal tip.*—Obtuse.
- *Number of ray flower.*—About 13.
- *Number of disk flower.*—About 127.
- *Diameter of pedicel of the first flower in a blooming period* (*the flower was attached to the top of a stem*).—About 1.2 mm.

*Length of pedicel of the first flower in a blooming period (the flower was attached to the top of a stem).*—About 4.5 cm.

*Number of flowers per flower cluster.*—About 97.

*Scent.*—Present.

Calyx:

*Degree of concavity.*—Flat.

*Degree of recurvature.*—About 2.2 mm.

*Color.*—Dark grayish brown (R.H.S.C.C. No. 200A) with a lot of anthocyanin at the base; light yellowish green (R.H.S.C.C.No. 139D) with little anthocyanin at the apex.

*Anthocyanin coloration.*—Present.

Pistil:

*Color.*—Deep reddish purple (R.H.S.C.C. No. 79B, J.H.S.C.C.No. 8907).

*Number.*—1.

*Type.*—the top of the style is splitted into two and the shape of the top is truncated.

Stamen:

*Color.*—Deep reddish purple (R.H.S.C.C.No. 79B, J.H.S.C.C.No. 8907).

*Type.*—5 anthers are connate, with separated filaments.

*Blooming period.*—End of November (Cutting in July).

Hardiness:

*Cold.*—Good.

*Heat.*—Good.

Resistance:

*Disease.*—Good.

*Insect.*—Good.

This new variety of Senecio genus plant named 'Sunsenereba' and *Senecio cruentus* have similar resistance to diseases (e.g. powdery mildew and leaf spot) and insects (e.g. aphid, whitefly and thrips). 'Sunsenereba' is a tall plant particularly suited for growing in pots.

The new and distinct variety of Senecio genus plant named 'Sunsenereba' was asexually reproduced by cutting a Hakushu-cho, Kitakoma-gun, Yamanashi-ken, Japan and the homogeneity and stability thereof were confirmed.

I claim:

1. A new and distinct variety of Senecio genus plant named 'Sunsenereba', substantially as herein illustrated and described.

* * * * *